United States Patent
Haldopoulos et al.

(10) Patent No.: US 6,780,309 B2
(45) Date of Patent: Aug. 24, 2004

(54) TAPERED HYDROPHOBIC FILTER FOR SUCTION CANISTERS

(75) Inventors: Dean Haldopoulos, Stone Mountain, GA (US); H. R. Buster Johnson, III, Tyler, TX (US)

(73) Assignee: Allegiance Corporation, McGaw Park, IL (US)

(*) Notice: Subject to any disclaimer, the term of this patent is extended or adjusted under 35 U.S.C. 154(b) by 0 days.

(21) Appl. No.: 10/104,350

(22) Filed: Mar. 22, 2002

(65) Prior Publication Data

US 2003/0178360 A1 Sep. 25, 2003

(51) Int. Cl.⁷ ............................ B01D 35/02; A61B 19/00
(52) U.S. Cl. ................. 210/97; 210/416.1; 210/448; 210/455; 210/497.01; 210/502.1; 422/101; 422/104; 604/319; 604/405
(58) Field of Search ............................ 604/319, 320, 604/321, 405, 406; 210/416.1, 500.29, 97, 100, 497.03, 435, 442, 444, 448, 455, 497.01, 502.1, 510.1; 422/101–102, 104

(56) References Cited

U.S. PATENT DOCUMENTS

| | | | |
|---|---|---|---|
| 3,809,085 A | | 5/1974 | Bidwell et al. ............. 128/275 |
| 4,184,963 A | * | 1/1980 | Sternberg ............... 210/321.87 |
| 5,032,116 A | | 7/1991 | Peterson et al. ........... 604/168 |
| 5,045,077 A | | 9/1991 | Blake, III ................... 604/321 |
| 5,053,132 A | * | 10/1991 | Sirkar ................... 210/500.23 |
| 5,080,983 A | | 1/1992 | Alexon et al. ................ 429/54 |
| 5,091,086 A | * | 2/1992 | Stengaard .................... 210/490 |
| 5,125,415 A | * | 6/1992 | Bell ........................... 600/579 |
| 5,156,811 A | * | 10/1992 | White ........................ 422/100 |
| 5,496,523 A | * | 3/1996 | Gazit et al. ................. 422/100 |
| 5,554,287 A | * | 9/1996 | Beck et al. ............ 210/500.29 |
| 5,603,900 A | | 2/1997 | Clark et al. ................. 422/101 |
| 5,630,939 A | * | 5/1997 | Bulard et al. ............ 210/416.1 |
| 5,725,516 A | | 3/1998 | Cook et al. ................. 604/319 |
| 5,776,260 A | | 7/1998 | Dunn et al. .................... 138/18 |
| 5,792,425 A | | 8/1998 | Clark et al. ................. 422/101 |
| 5,895,575 A | * | 4/1999 | Kraus et al. ................ 210/483 |

* cited by examiner

Primary Examiner—Terry K. Cecil
(74) Attorney, Agent, or Firm—Andrew G. Rozycki

(57) ABSTRACT

The invention described herein is drawn to a hollow cylindrical filter for use with a suction canister including a first portion having an open end and a first wall thickness, a second portion having a closed end and second wall thickness less than said first wall thickness, and an elongate central chamber having a substantially uniform diameter along its length. The filter is composed of a composite material including a porous plastic material and material adapted to increase the viscosity of a liquid coming into contact therewith. The filter is constructed to accommodate the changes associated with air flow velocity and shear force across the filter material as the fluid level in the canister rises, and automatically shuts off the vacuum to the interior environment of the suction canister. The invention also includes a filter system including such a filter in combination with a filter shield which accommodates the filter within and attaches to, or is alternatively integrated with, the underside of a suction canister lid.

11 Claims, 10 Drawing Sheets

$d_1 - d_2 = \Delta_d$

TAPERED HYDROPHOBIC FILTER FOR SUCTION CANISTERS

FIELD OF THE INVENTION

The invention relates to the field of medical suction canisters. In particular, the invention pertains to a filter and filter system for use in medical suction canisters.

BACKGROUND OF THE INVENTION

Suction canisters collect body fluids in association with medical procedures and treatments are known. Typical suction canisters contain a reservoir and a lid attached thereto. The lid can be constructed to have a patient port, tandem port, vacuum port and exit port. In operation, a vacuum source and associated tubing are attached to the vacuum port of the lid, which is sealed onto the reservoir in an airtight manner. Upon activation, the vacuum source draws fluid and/or air from the patient into the reservoir, where the fluid is collected. As the canister fills with the fluid, the fluid level approaches the underside of the canister lid. Preventing the fluid from contaminating the vacuum source and its associated tubing is an important aspect of suction canister devices so as not to contaminate the secondary equipment and the user, as well as prevent obstruction or interference of the equipment.

A variety of automatic shut-off mechanisms for medical suction canisters have been developed. Most of these devices involve mechanical closure mechanisms, such as floating ball valves, and the like.

Filters which are positioned in the vacuum flow path, which activate upon contact with fluid, are also known. Such filters can be constructed of composite materials comprising porous plastic and fluid barrier materials, such as carboxymethylcellulose. When such composite materials come into contact with liquid, the materials respond by creating a barrier thereby preventing air and liquid flow through the filter. Certain materials, such as carboxymethylcellulose, increase viscosity by hydrating and "gelling" upon contact with water. Upon completion of such "gelling", liquid and air flow are prevented from passing through the filter.

Several cylindrical hydrophobic filters having uniform interior diameters and uniform wall thickness are available. One example of such a filter is available from Domoch Medical Systems, Inc. (Riverside, Mo.), which has a cylindrical configuration having a constant outer diameter of about 1.05 inches (2.5 cm), a length of about 1.75 inches (4.45 cm), a uniform inner diameter of about 0.75 inches (1.9 cm), a uniform wall thickness of about 0.150 inches (0.4 cm), and a material volume of about 0.742 in$^3$(1.9 cm$^3$). Other hydrophobic cylindrical filters available from Abbott Laboratories, (Salt Lake City, Utah), DeRoyal Healthcare (Knoxville, Tenn.), and Allied Healthcare (St. Louis, Mo.) typically having a material volume of about 0.454 in$^3$ (1.15 cm$^3$). One disadvantage associated with currently available hydrophobic filters is their relatively large size and the amount of material used.

It would be advantageous to develop a hydrophobic, porous plastic filter for use in a suction canister which functions to automatically shut off air and fluid flow upon contact with a liquid. It would be even more advantageous to construct such a filter in a manner which is substantially effective but which has a smaller overall size and utilizes less material than currently available filters, thereby improves manufacturing efficiency.

SUMMARY OF THE INVENTION

The invention herein is a hydrophobic filter having a tapered hollow cylindrical configuration and adapted for use in medical suction canister systems. The filter of the invention comprises a variation in wall thickness along its length and is composed of a composite material comprising a porous plastic material and flow barrier material adapted to reduce and prevent air and liquid flow upon fluid contact therewith. The filter can be positioned in association with the lid of a suction canister system and between the vacuum source and reservoir of the canister.

The invention provides a hollow cylindrical filter for use in a suction canister comprising: a) first portion having an open end and a first wall thickness; b) a second portion having a closed end and a second wall thickness less than said first wall thickness; c) elongate central chamber having a substantially uniform diameter along its length; and wherein said filter is composed of a composite material comprising a porous plastic and a flow barrier material adapted to reduce and prevent air and liquid flow upon contact with a fluid.

The invention also provides a filter system for use in a suction canister having a lid and reservoir, the filter system comprising a hollow cylindrical filter and a filter shield. The filter shield functions both to reduce the likelihood of premature fluid contact on the filter from the lateral direction, and to attach the filter onto the underside of the suction canister lid. The filter shield for use with a suction canister having a lid and reservoir comprises: an outer portion and inner portion, each having a top and bottom portion, said inner portion having an inner sidewall and said outer portion having an outer sidewall; a shield chamber located within said inner portion and open at both ends; wherein the filter shield is adapted to attach to the underside of said suction canister lid; and wherein said shield chamber is adapted to receive and retain a hollow cylindrical filter within such that said inner sidewall laterally circumscribes said filter while exposing one end of the filter. In a preferred embodiment, the dimensions of the shield chamber accommodate the entire length of the filter when positioned within the filter shield. In an alternative embodiment, the filter shield can be integrally constructed as part of the lid.

BRIEF DESCRIPTION OF THE DRAWINGS

The invention is further illustrated by the drawings as follows.

DETAILED DESCRIPTION OF THE INVENTION

The term "substantially uniform" as used herein within the context of the central chamber dimensions of the filter, is meant to indicate that the diameter of the chamber remains relatively constant throughout filter chamber length despite variations in wall thickness of the first and second portions of the filter.

The term "cylindrical" as used herein is meant to refer to the general overall shape of the filter of the invention. The term is, however, not intended to imply constant or uniform exterior diameter of the filter.

The terms "fluid" and "liquid" as used herein are meant to refer to aqueous-based fluids capable of reacting with the filter material in such a manner as to initiate the intake barrier function of the filter. The terms are meant to include water, blood, urine, body fluids, and other fluids typically associated with surgical procedures. The terms are not meant to include compounds or compositions which would degrade or decompose or render the filter material inoperative within the context of the invention.

The hollow cylindrical filter and filter shield according to the invention is adapted for use in conjunction with a suction canister. Suction canisters which can be used with the invention include medical suction canisters having overall basic lid and reservoir construction, and cooperate with a vacuum source and its associated equipment, e.g., tubing and the like. In use and when the vacuum source is activated, air and fluids from a patient's body are drawn into a suction canister through a "patient" port on the lid and into a reservoir attached to the lid, the suction being effected via a "vacuum port" through the lid. Suction canisters are typically used in conjunction with medical procedures and treatments which involve the removal of air and fluids from a patient's body. Generally, suction canister lids can also contain "tandem" ports and pour spouts. Each port can be adapted to removably attach secondary equipment, such as tubing and the like.

Figure 1:
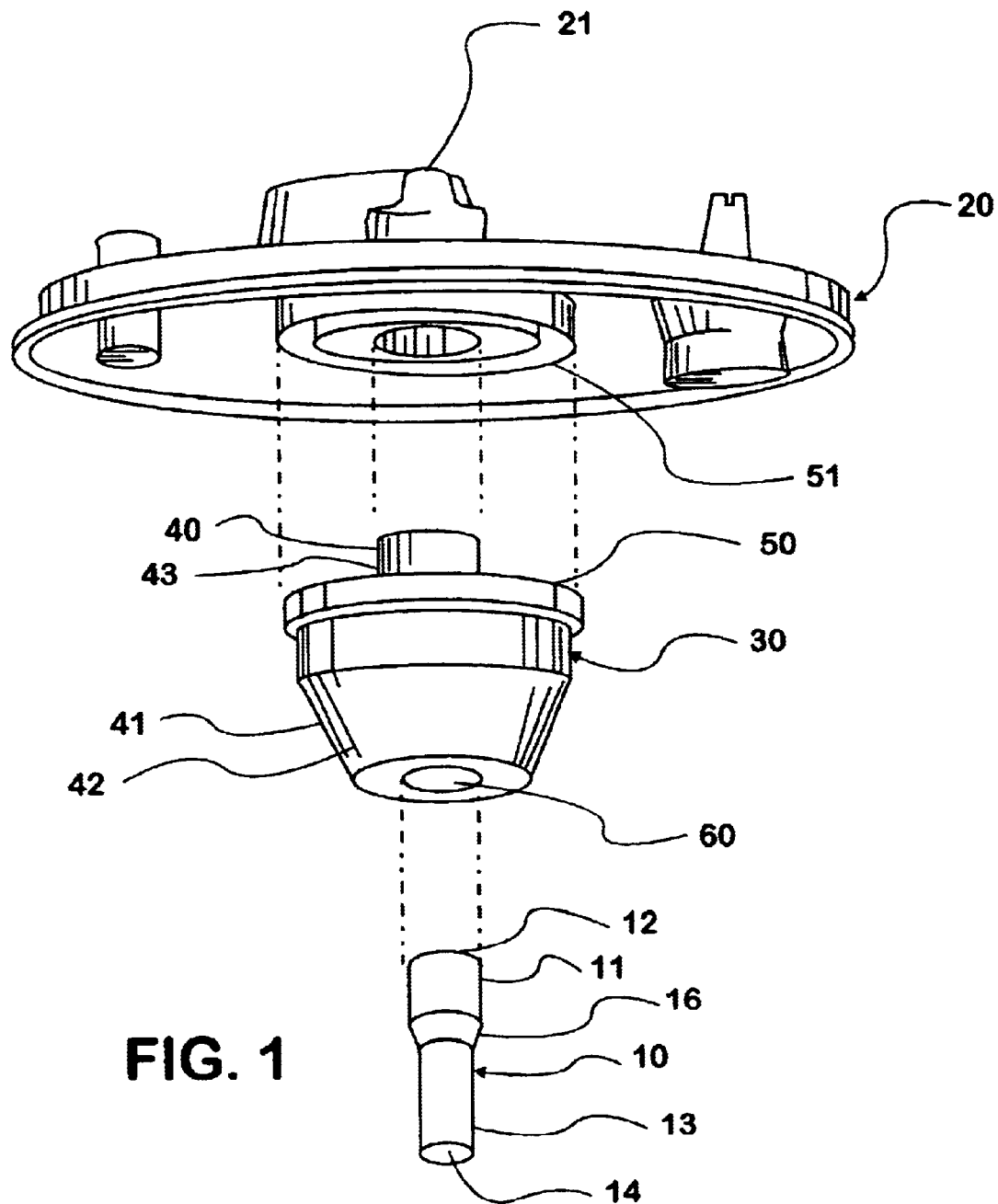
FIG. 1 is an exploded view of a suction canister lid containing the filter and filter shield in accordance with one embodiment of the invention.
Figure 2:
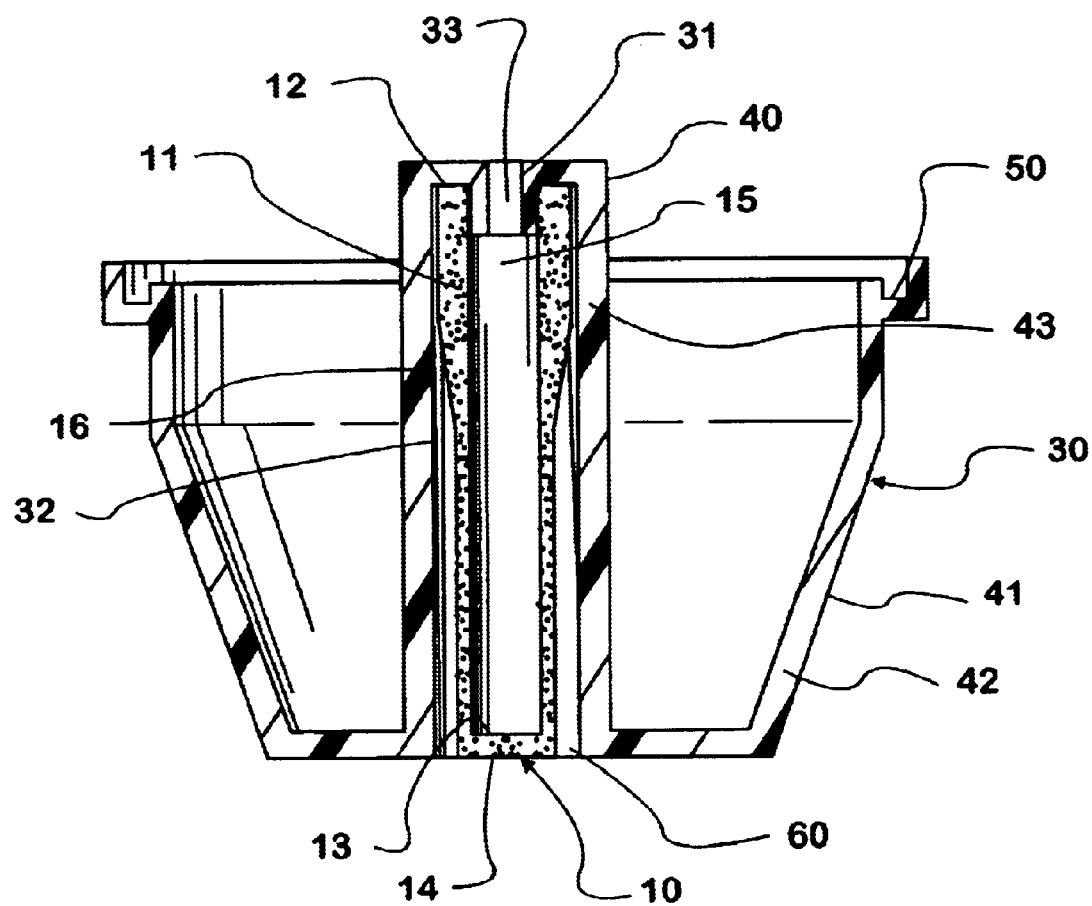
FIG. 2 is a cross-sectional side view a filter system comprising a filter shield with a filter residing therein in accordance with one embodiment of the invention.

Referring now to FIG. 1, the filter 10 of the invention is adapted to be positioned within the conduit or passageway of a suction canister lid 20, particularly the underside of the lid, such that air flow (and eventually fluid) contacts the filter 10 at the flow path into the vacuum port 21 such that the filter 10 precedes the vacuum source and its associated tubing (not shown). The filter 10 in its "dry" state permits the passage of air through the filter from the interior canister environment and into the vacuum port 21 and environment beyond the lid 20. The filter 10 of the invention can be coupled either directly or indirectly onto the underside of the lid 20. One aspect of the invention includes a filter shield 30, which functions to both control the sequence of fluid contact to the filter 10 and secure the filter 10 to the underside of the lid 20. In one embodiment and as shown in FIG. 1, the filter 10 and filter shield 30 of the invention are assembled by inserting the filter 10 in a longitudinal direction into the filter shield 30 and attaching the filter shield 30 and filter 10 (as depicted in FIG. 2) to the underside of the suction canister lid 20. Alternatively, the filter shield 30 can be attached to the canister lid 20 first, and the filter 10 inserted therein after. The lid 20 can then be attached to the rim of the reservoir (not shown). In the case of the alternative embodiment wherein the filter shield is integrated as part of the lid, there is no filter shield attachment step. Associated tubing and attachments can be affixed onto various ports and openings of the lid, such as a tubing for a tandem port, a cap for a pour spout, vacuum tubing to the vacuum port, and tubing from the patient to the patient port.

Figure 3:
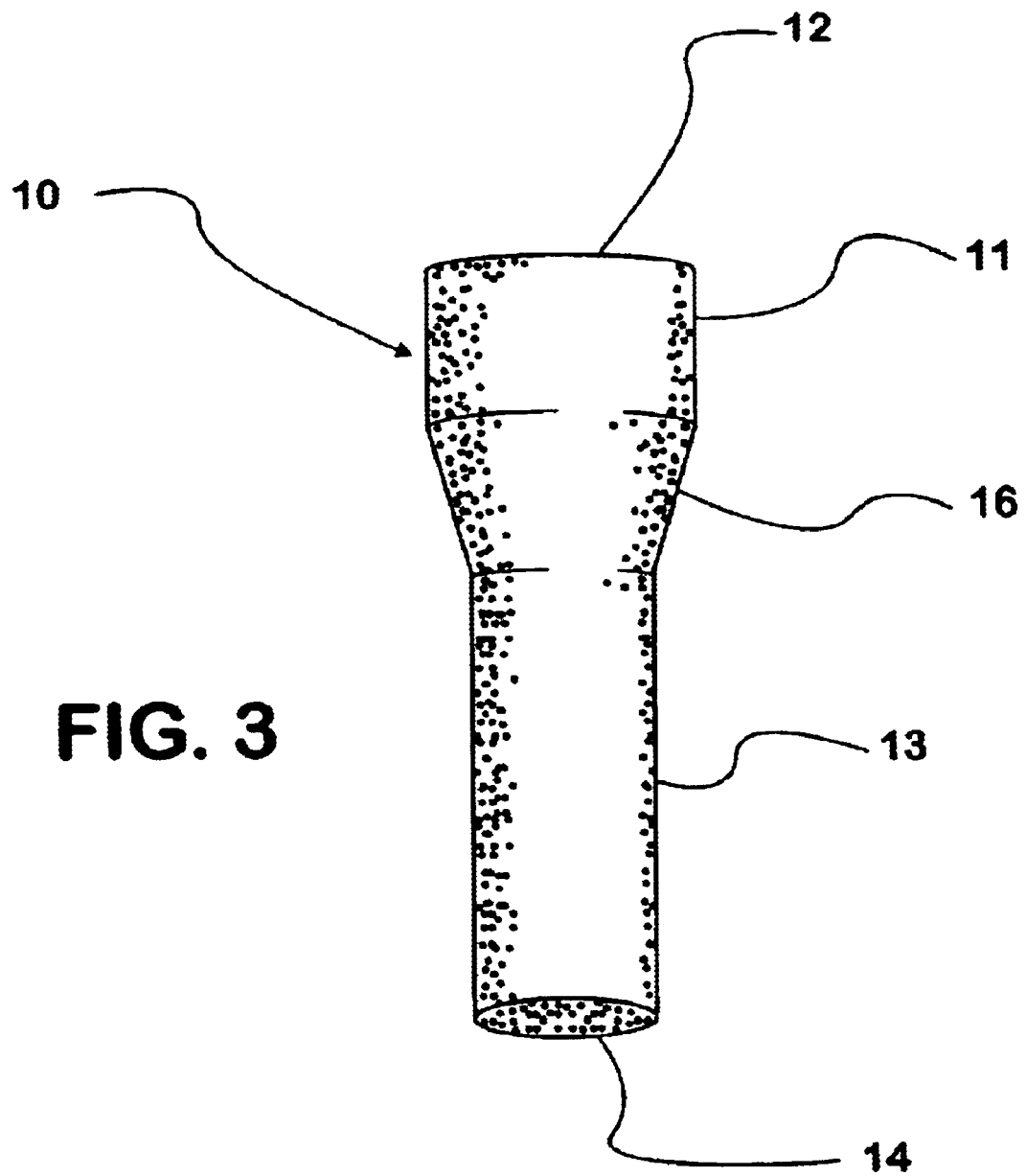
FIG. 3 is an angled side view of a filter in accordance with one embodiment of the invention.
Figure 4:
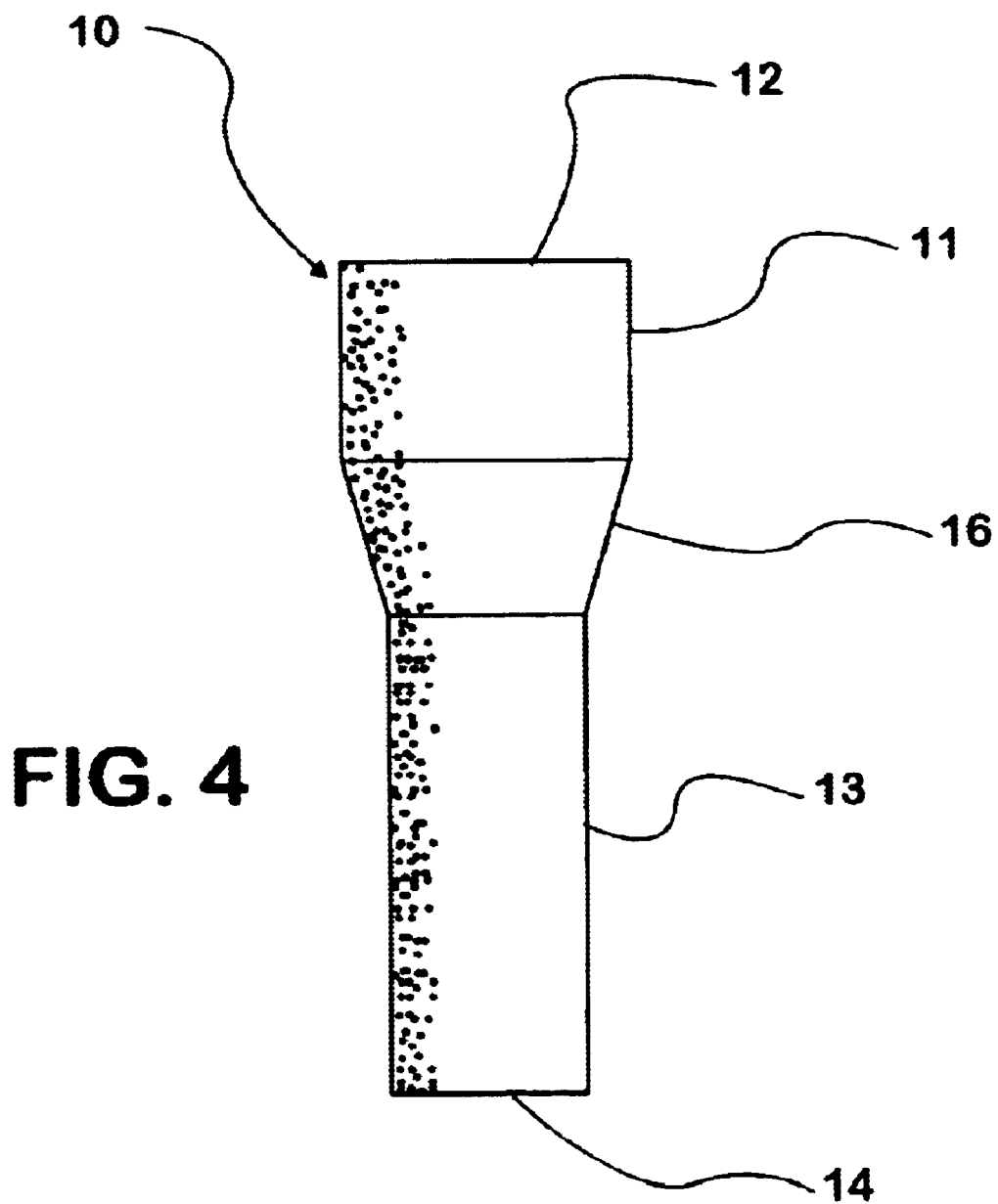
FIG. 4 is a side view of the filter in accordance with one embodiment of the invention.
Figure 5:
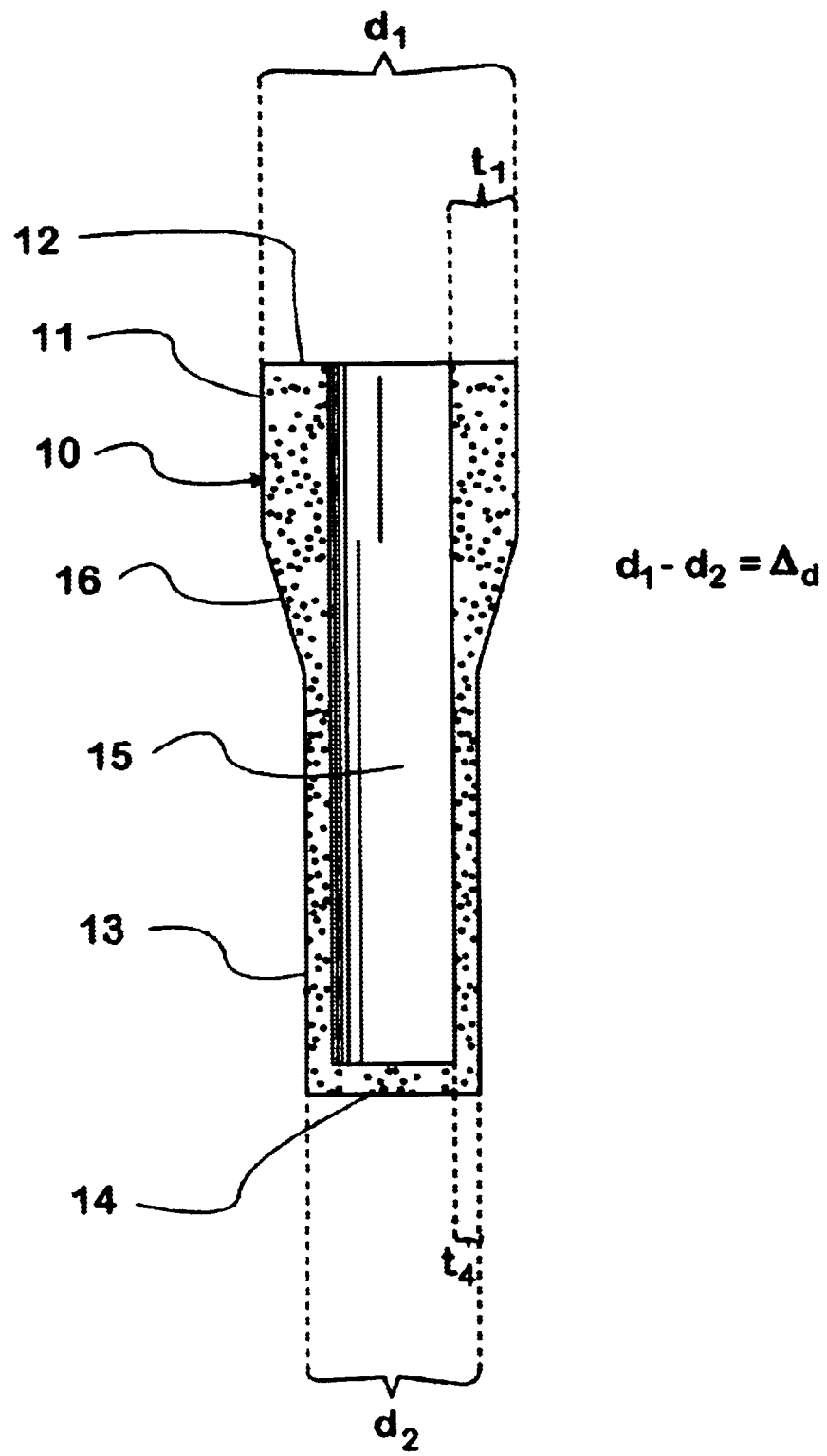
FIG. 5 is a cross-sectional side view of the filter in accordance with one embodiment of the invention.

Referring now to FIGS. 3 through 7, the filter 10 of the invention generally comprises a hollow, tubular configuration which is composed of, at least in part, a composite material comprising porous plastic material and a flow barrier material. As shown in FIGS. 3, 4 and 5, the filter 10 comprises a first portion 11 having an open end 12 and a first wall thickness $t_1$ (see FIG. 5), a second portion 13 having a closed end 14 and a second wall thickness $t_2$ which is less than said first wall thickness $t_1$, and an elongate central chamber 15 having a substantially uniform diameter along its length. The first portion 11 having an open end 12 is adapted to cooperate with a filter attachment structure (see FIGS. 2 and 10) on the filter shield 30, and it is this end of the filter 10 which, when positioned, is in closest proximity to the vacuum port 21 and vacuum source (not shown). One embodiment of a filter attachment structure is shown as a hollow extension 31 located at the inner portion 40 of the filter shield 30 extending inward within a shield chamber 60 and adapted for insertion into the elongate central chamber 15 of the filter 10 through the open end 12 of the first portion 11 of the filter 10. When assembled and attached to a suction canister system, the hollow extension 31 permits free air flow between the interior environment of the filter 10 and the vacuum port 21 of the canister lid 20.

Another filter attachment structure, which can be present by itself or in addition to the hollow extension 31 of the filter shield 30, can be in the form of a plurality of inner sidewall extensions 32 in the inner portion 40 protruding inward within the shield chamber 60.

Figure 6:
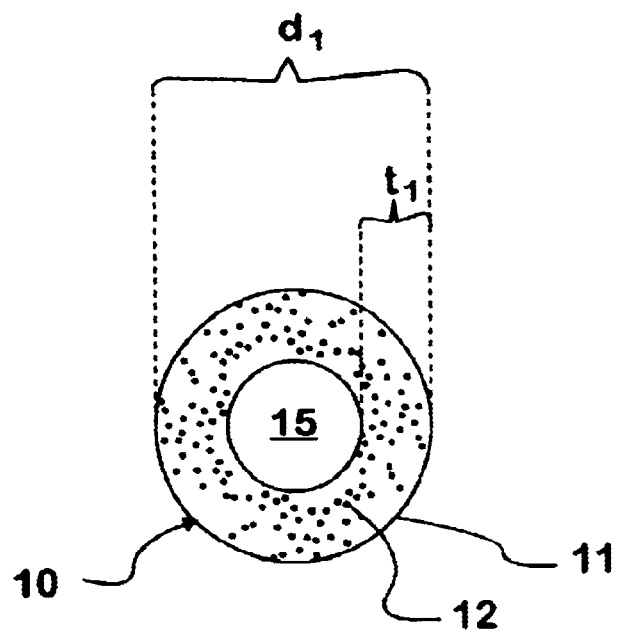
FIG. 6 is a top view of the filter in accordance with one embodiment of the invention.
Figure 7:
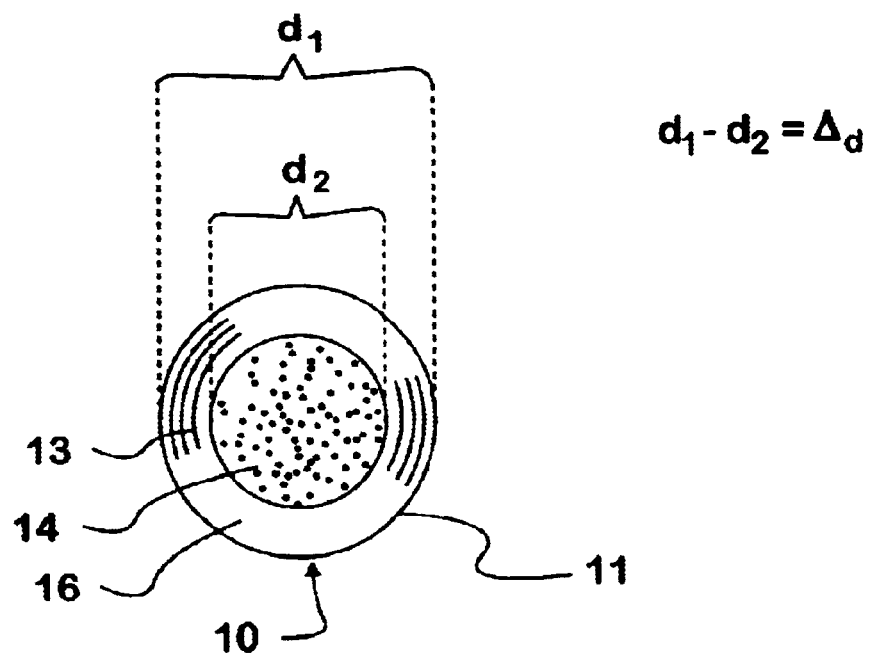
FIG. 7 is a bottom view of the filter in accordance with one embodiment of the invention.
Figure 8:
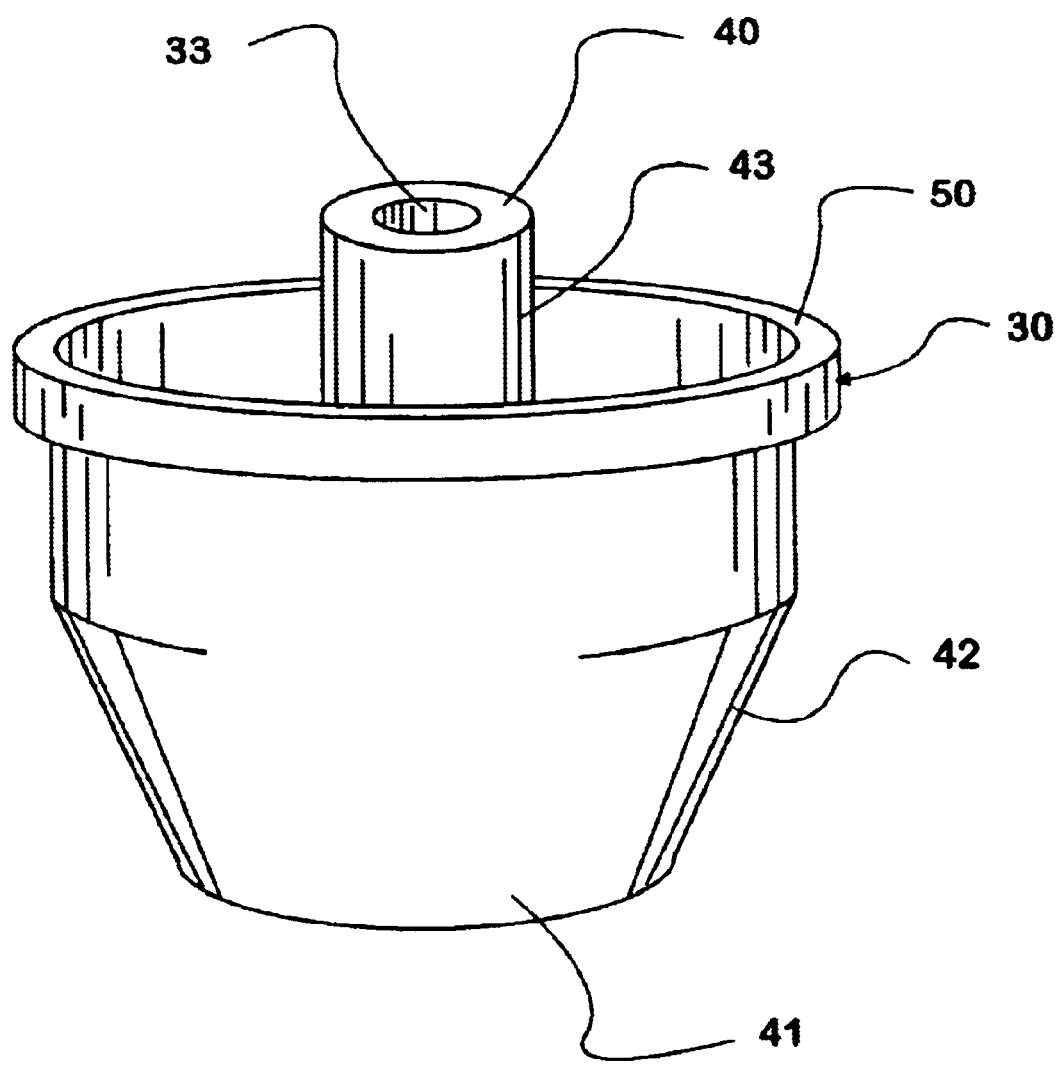
FIG. 8 is an angled side view of the filter shield according to one embodiment of the invention.
Figure 9:
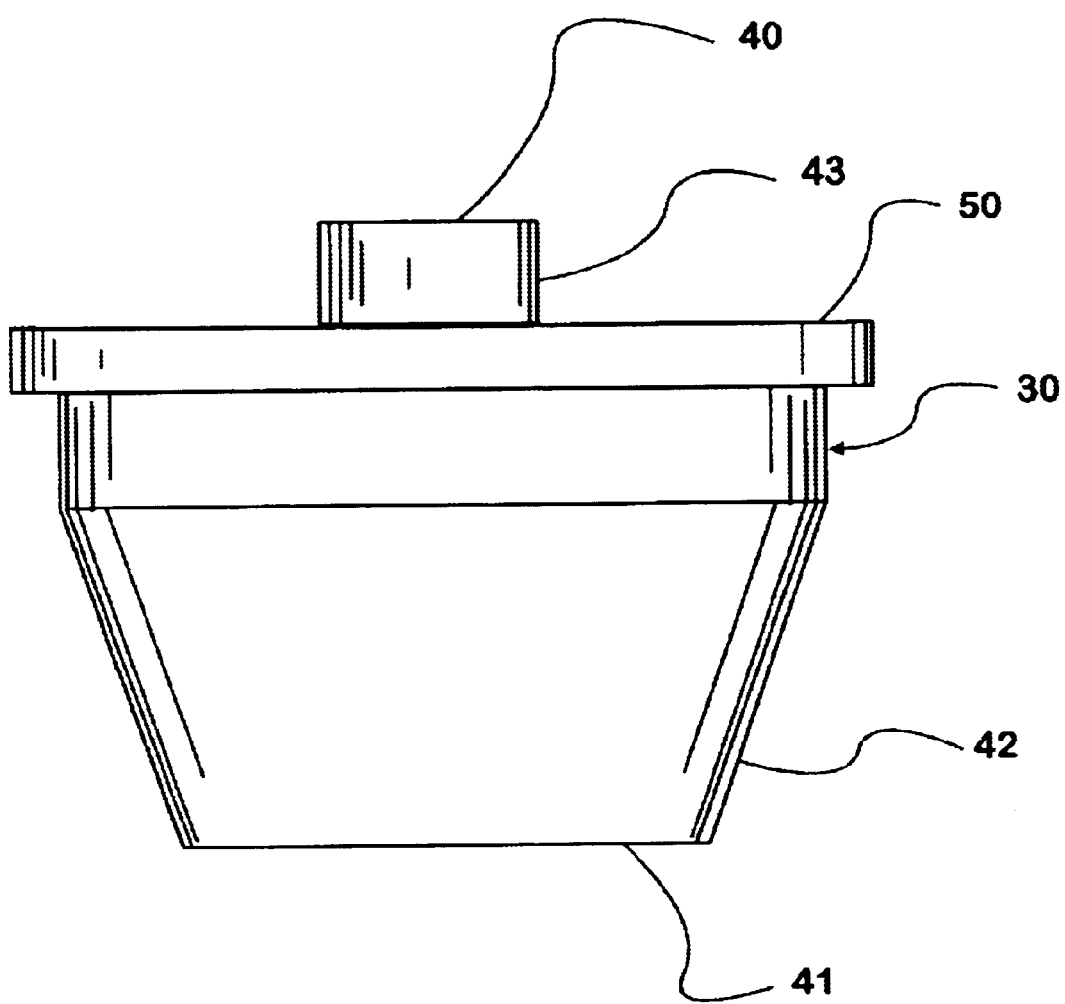
FIG. 9 is a side view of the filter shield according to one embodiment of the invention.

Referring now to FIGS. 5, 6, and 7, the elongate central chamber 15 of the filter has a substantially uniform diameter along its length from the open end 12 of the first portion 11 to the closed end 14 of the second portion 13. The outer diameter $d_1$ of the first portion 11 of the filter 10, however, is greater than the outer diameter $d_2$ of the second portion 13. In other words, the wall thickness between the first and second portions of the filter varies such that the wall thickness $t_1$, of the first portion 11 is greater than the wall thickness $t_2$ of second portion 13. The total difference in wall thickness between the two portions of the filter 10 is depicted as $\Delta_d$, calculated from the difference between $d_1$ and $d_2$.

In a preferred embodiment of the invention and as shown in FIGS. 1 through 5, the exterior of the filter 10 is configured such that first portion 11 and second portion 13 are cylindrical with a middle frusto-conical region 16 located therebetween. Accordingly, there is a gradient of wall thickness between the first and second portions in the form of a distinctive taper. Alternatively, the adjustment in wall thickness from the first portion to the second portion can be a circumscribing stepped configuration or a gradual smooth taper.

An important aspect of the invention is the overall configuration of the filter. The gradient in wall thickness offers advantages to the filter function. As the filter material contacts fluid, the composite material blocks air transport through the contacted region of the filter. The remaining "dry" region of the filter contains a reduced surface area for air flow to permeate the filter material, thereby causing an increase in air flow velocity through the dry region of the filter. The portion of the filter which first comes into contact with fluid is the second portion. The first portion of the filter, therefore, has a greater wall thickness as compared to the second portion. The first portion of the filter experiences the increased air flow velocity after the second portion has formed a flow barrier, by hydrating and "gelling", or otherwise creating an obstruction to the passage of air and liquid through the filter. The increase in flow velocity facilitates the hydrated flow barrier material penetration depth into the filter while maintaining the overall structural integrity of the filter.

As such, the filter is designed to accommodate the changing physical forces exerted against the filter in cooperation with the changing physical state of the filter material. As a result, the filter of the invention can accomplish substantially the same effectiveness of function but with reduced size and less material as compared to conventional cylindrical filters with uniform inner diameters and thicknesses. The dimensions of the filter of the invention can vary provided the inventive features, e.g., first and second portion with greater first portion wall thickness, are present. In one embodiment, the filter according to the invention has a length of about 1.6 inches (4.06 cm), a uniform inner diameter of about 0.290 inches (0.73 cm), a first portion outer diameter $d_1$ of about 0.550 inches (1.4 cm) and wall thickness $t_1$ of about 0.130 inches (0.33 cm); and a second portion outer diameter $d_2$ of about 0.470 inches (1.19 cm) and a wall thickness $t_2$ of about 0.090 inches (2.3 mm).

In accordance with the invention, the filter material can be composed of a composite material comprising a porous plastic material and flow barrier material adapted to respond to contact with fluid. A variety of porous plastic materials and flow barrier materials can be used. Suitable porous plastic materials include, but are not limited to, polyethylene. Porous plastic materials by themselves can permit the transport of air while inhibiting the transport of water or other liquids through. Upon encountering water, the porous plastic material alone functions as a fluid barrier to some extent.

Suitable flow barrier materials adapted to respond to contact with fluid can include materials adapted to hydrate upon liquid contact. Suitable materials adapted to hydrate upon liquid contact include, but are not limited to, cellulose derivatives, starch and starch derivatives, and polymers. A preferred cellulose derivative for use in the invention is carboxymethylcellulose (a.k.a. CMC). One example of carboxymethylcellulose which can be used is Carbose D™, available from PennCarbose, Inc., Somerset, Pa. Carboxymethylcellulose is a preferred flow barrier material because of its rapid reactivity and effective sealing properties for fluid flow.

One composite material which can be used as the filter material in accordance with the invention is blended and sintered combination of polyethylene and carboxymethylcellulose. When fluid contacts carboxymethylcellulose, the carboxymethylcellulose goes into solution, hydrates, swells, and becomes viscous. The hydration rate increases as greater shear force is applied to the advancing dry-hydrated interface via increased flow velocity, such as that caused by exerted vacuum forces. The viscosity of the gel increases quickly to the point where air and fluid penetration through the porous plastic material of the filter material ceases.

Starch and starch derivatives can be used as the flow barrier material in conjunction with the porous plastic material in accordance with the invention as well. Similarly, starch and starch derivatives can absorb liquid and hydrate, thereby swelling and blocking flow paths through the porous plastic material.

In an alternative embodiment, the flow barrier material can be in the form of a coating on the exterior surface of the filter. Similarly, the flow barrier material interacts with fluid and is altered by virtue of the fluid contact to resist fluid penetration through the filter wall.

The filter material composite can include porous plastic material together with combinations of two or more different flow barrier materials. For example, the composite can comprise porous plastic and a combination of carboxymethylcellulose and starch or starch derivative.

The filter can be prepared using conventional molding and forming equipment and techniques readily available in the art. Accordingly, the filter can be prepared using a sintering and molding procedure. In accordance with one procedure, a powder mixture of dry resin and flow barrier material, e.g., carboxymethylcellulose is poured into a mold. The powder preferably contains a wide melt index, thereby facilitating control over the soft state of the powder before reaching a liquid state upon increasing temperature. The mold contains the dimensions to produce a filter having the final dimensions desired. After being filled with the powder, the mold is capped-off. The powder is heated only up to the soft state to fuse the particles thereby agglomerating and creating the porous "foam" structure. Temperature control is critical to the process, since temperatures too high can completely liquify the composition creating an impervious solid material upon cooling. The exterior surface of the resin particles soften and fuse with one another while the particle center remains unaltered. Upon cooling and removing from the mold, the filter composite is formed and shaped according to the mold, the plastic particles being aggregated with the flow barrier material in the spaces between.

The filter system of the invention comprising a hollow cylindrical filter as described herein together with a filter shield 30 which is adapted to receive and retain the filter 10 within as shown in FIGS. 1 and 2. Now referring to FIGS. 8 through 12, the filter shield 30 is adapted for use with a suction canister having a lid 20 and reservoir (not shown). The filter shield 30 comprises an inner portion 40 and outer portion 41, an outer sidewall 42 and an inner sidewall 43. The inner portion 40 contains a lid attachment structure and vacuum port opening 33 positioned in alignment with the vacuum port 21 of the suction canister lid 20 (as shown in FIG. 1). The lid attachment structure can take a variety of forms provided the filter shield can be secured to the underside of the lid. In one embodiment and as depicted in FIGS. 1, 8, 10 and 12, the lid attachment structure is in the form of a rim 50 adapted to mate with a corresponding receiving rim 51 (see FIG. 1) on the underside of the lid 20.

In an alternative embodiment, the filter shield can be integral with the suction canister lid. The filter shield can be permanently attached by bonding to the underside of the canister lid, or integrally molded as part of the lid.

The overall dimensions and shape of the filter shield can vary. For illustrative purposes, the filter shield is depicted in the figures as having a tapered cylindrical "cup" configuration. The filter shield can be composed of any suitable plastic material and constructed using conventional molding equipment and techniques readily available in the art. The filter shield can be constructed as an integrally molded, single piece.

Figure 10:
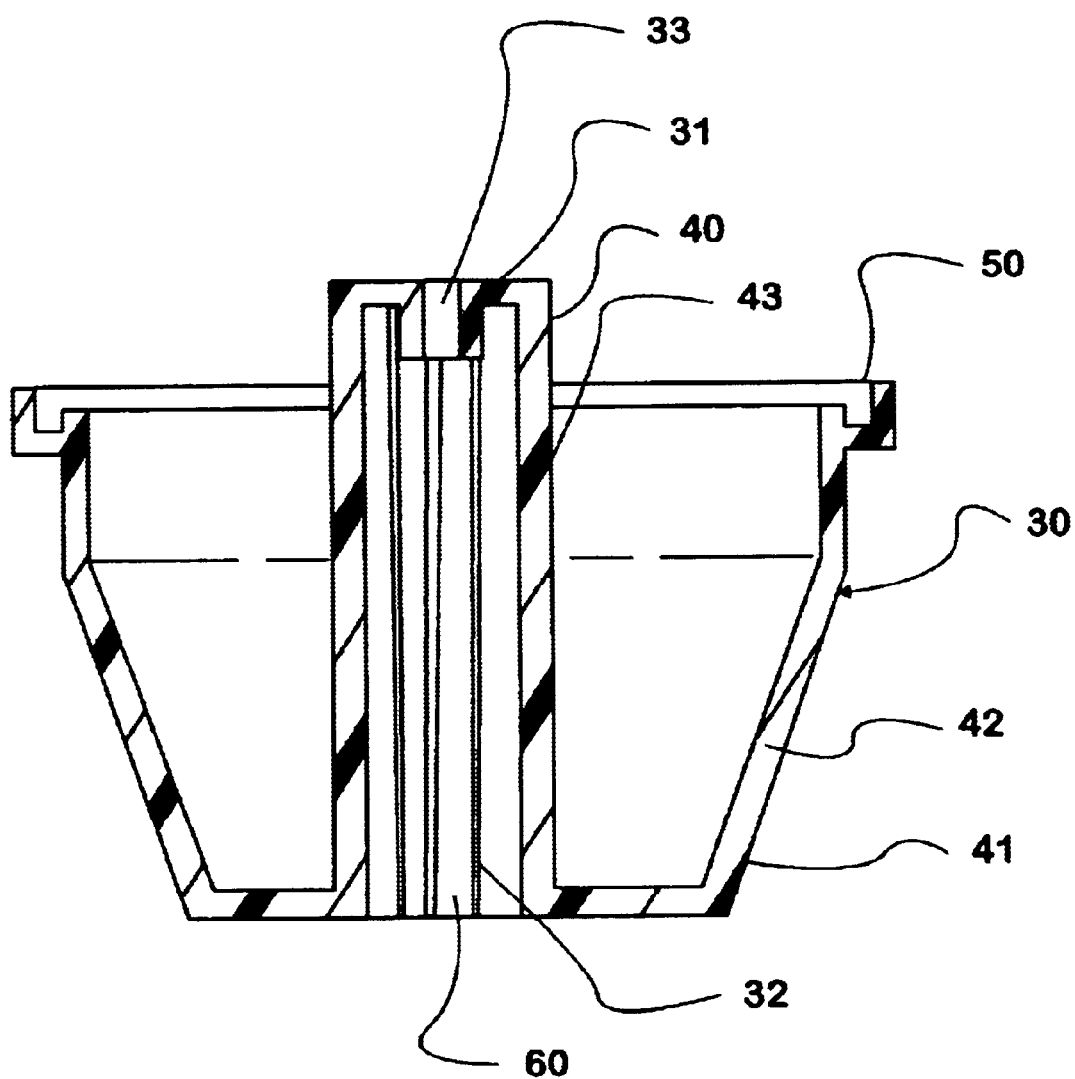
FIG. 10 is a cross-sectional side view of the filter shield according to one embodiment of the invention.
Figure 11:
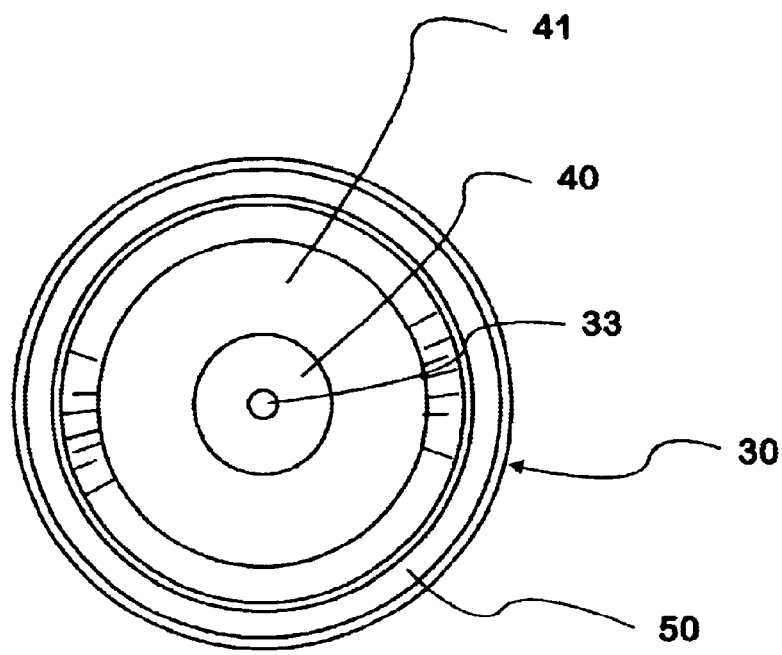
FIG. 11 is a top view of the filter shield according to one embodiment of the invention.
Figure 12:
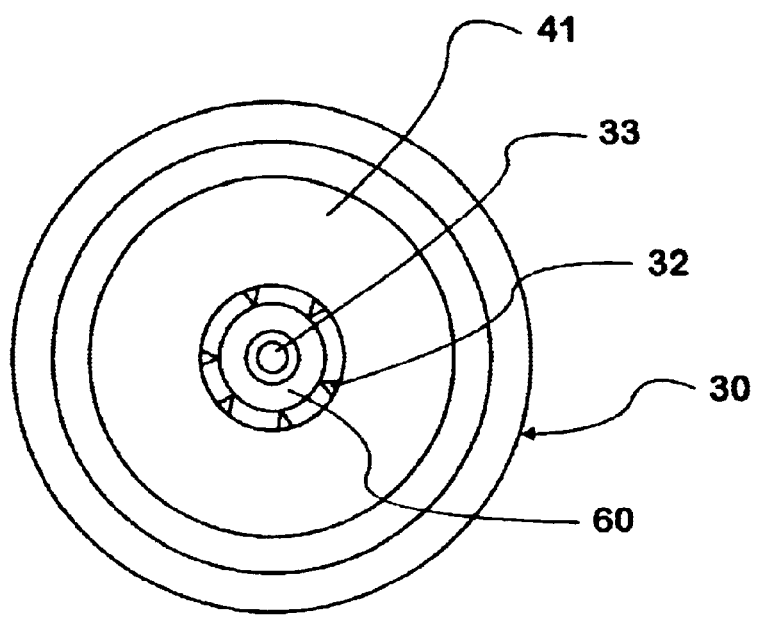
FIG. 12 is a bottom view of the filter shield according to one embodiment of the invention.

Now referring to FIGS. 2 and 10, the shield chamber 60 is located within the inner portion 40 between the top and bottom and within the inner sidewall 43. The shield chamber 60 is open at both ends and adapted to receive and retain a hollow cylindrical filter 10 within. In addition to having a vacuum port opening 33 on the end of the inner portion 40 which is intended to be closest to the lid, the inner portion 40 of the filter shield 30 further comprises a filter attachment structure.

In the figures, the filter attachment structure is shown as a hollow inward extension 31 adapted to mate with the open end 12 of the first portion 11 of the filter 10, in combination with a plurality of inner sidewall extensions 32 protruding from the inner sidewall 43 surface of the inner portion 40 and adapted to compress the exterior of the filter when positioned within the shield chamber 60. Inner sidewall extensions 32 can take a variety of forms, structures and configurations, provided the structural form creates a secure fit which inhibits unintentional migration of the filter 10 within the filter shield 30. For illustrative purposes, the inner sidewall extensions 32 are shown as intermittently-spaced elongate ridges (as shown in FIG. 10) which extend inward to create a gradually decreasing diameter toward the top of the inner portion 40 and vacuum port opening 33 of the filter shield 30. Other examples of suitable inner sidewall extensions which can be used can include a tapered inner sidewall diameter, one or more inwardly extending rings, nodules, prongs, friction-enhanced surfaces, and the like. When the suction canister system is completely assembled and the vacuum source activated, the filter 10 is further held in place by the applied vacuum forces as well.

In a preferred embodiment, the dimensions of the inner portion 40 of the filter shield 30 are designed to house and laterally circumscribe substantially the entire filter length placed within while leaving the closed end 14 of the second portion 13 of the filter exposed and oriented toward the interior environment of the suction canister. In accordance with this preferred design, the sides of the filter are protected against premature or unintentional fluid contact from splashing, for example. Furthermore, the preferred design ensures that the closed end of the second portion of the filter is the first portion of the filter to initially contact fluid as the fluid level within the reservoir rises.

Referring again to FIG. 1, the filter 10 of the invention can be inserted into the shield chamber 60 of the filter shield 30 and secured therein. The filter system, e.g., filter and filter shield assembly, can then be secured to the underside of the suction canister lid 20. The canister lid 20 can then be attached to the suction canister reservoir (not shown), and the associated tubing and equipment attached to the various ports and components on the upper surface of the lid in accordance with the canister design used. Before or during a medical procedure employing suction, the vacuum source (not shown) is activated thereby drawing air and fluid into the suction canister through a patient intake port. Air exits the suction canister through the filter and vacuum port while fluids are collected within the reservoir (not shown).

Once the fluid level rises and comes into contact with the exposed second portion 13 of the filter 10, the fluid encounters the filter material comprising the porous plastic material and flow barrier material. After initial contact with a fluid, the filter 10 is altered such that it comprises "wet" and "dry" regions, with the wet hydrated region advancing in area toward the first portion 11 of the filter 10. Accordingly, the remaining unaltered "dry" region of the filter 10 experiences increased air flow velocity, and the shear force at the dry-hydrated interface region of the filter increases. The increasing shear force increases the hydration rate of the flow barrier material. The filter of the invention accommodates the changing flow velocity and shear forces via the increasing wall thickness toward the first portion 11 of the filter 10. Thus, the thicker filter wall provides greater structural resistance to the increasing flow forces toward the "shut-off" point of the vacuum. Eventually, the entire filter is saturated, thereby preventing flow of air and liquid through the filter and shutting off the vacuum function from the suction canister environment.

By virtue of the inventive and efficient filter design, the filter of the invention affords effective filter function using less filter material and reduced overall size as compared to relatively larger filters having uniform wall thickness. The invention therefore accomplishes an efficient hydrophobic filter function per reduced filter material volume. As a result, an overall material volume of about 0.202 in$^3$ (0.51 cm$^3$) can be used for filters prepared in accordance with the invention, as compared to filter material volumes about 2 to 3 times greater of conventional hydrophobic filter designs.

Industrial Applicability

The filter and filter system of the invention is useful as part of a suction canister system for a medical procedure, for example, wherein such a procedure involves the controlled collection of fluids from a patient and prevention of contact of such fluids with a vacuum system and associated equipment is desired. The filter automatically shuts off air and fluid flow in suction canister systems when fluids have attained a predetermined level, thereby reducing the need for monitoring such during the procedure. Furthermore, the efficient design of the filter and filter system of the invention affords an effective filter function which accommodates changing forces during its use, and which uses relatively less material and therefore reduced manufacturing costs.

The invention has been described with reference to various specific and preferred embodiments and techniques. It will be understood, however, that reasonable variations and modifications of such embodiments and techniques are possible without significantly departing from either the spirit or scope of the invention.

What is claimed is:

1. A hollow cylindrical hydrophobic filter structured for use in a medical fluid collection and suction canister comprising:
    (a) first portion having an open end and a first wall thickness;
    (b) a second portion having a closed end and a second wall thickness less than said first wall thickness;
    (c) an elongated central chamber having a substantially uniform diameter along its length; and
    wherein both said first and second filter portions are composed of a composite material comprising a porous plastic material and a flow barrier material adapted to hydrate in response to contact with fluid thereby preventing fluid flow through the hydrated portion, said filter configured such that the increasing hydration of the filter ultimately prevents flow through the suction canister.

2. The hollow cylindrical filter of claim 1, wherein the filter further comprises a frust-conical region located between said first portion and second portion.

3. The hollow cylindrical filter of claim 1, wherein the porous plastic material comprises polyethylene.

4. The hollow cylindrical filter of claim 1 wherein said flow barrier material adapted to hydrate upon fluid contact comprises a cellulose derivative.

5. The hollow cylindrical filter of claim 4 wherein said flow barrier material adapted to hydrate upon fluid contact comprises carboxymethylcellulose.

6. The hollow cylindrical filter of claim 1 wherein said flow barrier material adapted to hydrate upon fluid contact comprises a starch or a starch derivative.

7. The hollow cylindrical filter of claim 1 wherein said flow barrier material is in the form of a coating on the exterior surface of said filter.

8. The hollow cylindrical filter of claim 1 wherein said flow barrier material comprises a combination of a cellulose derivative and a starch or starch derivative.

9. The hollow cylindrical filter of claim 1, wherein the filter has a length of about 1.6 inches (4.06 cm), a uniform inner diameter of about 0.290 inches (0.74 cm), a first portion outer diameter $d_1$ of about 0.550 inches (1.4. cm) and wall thickness $t_1$ of about 0.130 inches (0.33 cm); and a second portion outer diameter $d_2$ of about 0.470 inches (1.19 cm) and a wall thickness $t_2$ of about 0.090 inches (2.3 mm).

10. A filter system structured for use with a medical fluid collection and suction canister comprising the filter of claim 1 in combination with a filter shield, said filter shield comprising:
   a) an inner portion and an outer portion, each having top and bottom portions, said inner portion having an inner sidewall and said outer portion having an outer sidewall;
   b) a shield chamber located within said inner portion, the shield chamber being open at both ends;
   wherein said filter shield is structured to attach to the underside of a suction canister lid; and
   wherein said shield chamber is structured to receive and retain a hollow cylindrical filter within such that said inner sidewall laterally circumscribes substantially the entire length of said filter and exposes the closed end of said filter.

11. A filter system structured for use with a medical fluid collection and suction canister comprising the filter of claim 1 in combination with a filter shield, said filter shield comprising:
   a) an inner portion and an outer portion, each having top and bottom portions, said inner portion having an inner sidewall and said outer portion having an outer sidewall;
   b) a shield chamber located within said inner portion, the shield chamber being open at both ends;
   wherein said filter shield is integrated with the underside of a suction canister lid; and
   wherein said shield chamber is adapted to receive and retain a hollow cylindrical filter within such that said inner sidewall laterally circumscribes substantially the entire length of said filter and exposes the closed end of said filter.

* * * * *